United States Patent [19]
Wheeler

[11] Patent Number: 5,885,262
[45] Date of Patent: Mar. 23, 1999

[54] WASTE BAG

[75] Inventor: Raymond Wheeler, Brandon, England

[73] Assignee: Guardline Disposables Limited, United Kingdom

[21] Appl. No.: 819,843

[22] Filed: Mar. 17, 1997

[51] Int. Cl.⁶ .................................................. A61M 1/00
[52] U.S. Cl. .................... 604/327; 156/580.1; 156/73.1; 383/221; 383/116; 383/113; 383/109
[58] Field of Search ..................................... 604/327, 331, 604/349, 352; 383/113, 116, 221, 109; 493/223; 156/73.1, 580.1, 221, 227, 73.4

[56] References Cited

U.S. PATENT DOCUMENTS

| | | | |
|---|---|---|---|
| 2,991,001 | 7/1961 | Hughes | 383/211 |
| 3,292,626 | 12/1966 | Schneider | 604/352 |
| 3,523,537 | 8/1970 | Hill | 604/352 |
| 3,593,622 | 7/1971 | Sengewald | 493/223 |
| 4,292,609 | 9/1981 | Erickson | 428/246 |
| 4,820,291 | 4/1989 | Terauchi et al. | 604/349 |
| 4,886,509 | 12/1989 | Mattson | 604/349 |
| 4,890,936 | 1/1990 | Cooper | 383/109 |
| 5,476,323 | 12/1995 | Gold | 383/211 |

*Primary Examiner*—Robert A. Clarke
*Attorney, Agent, or Firm*—William A. Drucker

[57] ABSTRACT

A waste bag made from a sheet of plastics laminate comprising a layer of generally fluid-proof plastics material and a layer of liquid-absorbent plastics material. The liquid-absorbent material is on the inside of the bag, and the laminate is turned back on itself along at least one seam of the bag. Regions of the generally fluid-proof plastics material that are in contact with one another along that seam are sealed together ultrasonically.

10 Claims, 4 Drawing Sheets

WASTE BAG

The present invention relates to a waste bag, which has a liquid-absorbent material on its inside. Such a bag is especially useful, for example in disposing of medical waste which may include body fluids.

One previously proposed such waste bag is described in EP-B-0 317 047. The waste bag described in that prior specification has an internal lining of a liquid-absorbent material which terminates inwardly of the mouth of the bag to enable that region to be gathered and tied.

One disadvantage in this construction of bag is the difficulty experienced in its manufacture, especially if the lining is made separately from the outer material of the bag.

A first aspect of the present invention seeks to provide a remedy.

Accordingly, the first aspect of the present invention is directly to a waste bag made from a sheet of plastics laminate comprising a layer of generally fluid-proof plastics material and a layer of liquid-absorbent plastics material, in which the liquid-absorbent material is on the inside of the bag, and the laminate is turned back on itself along at least one seam of the bag, and regions of the generally fluid-proof plastics material that are in contact with one another along that seam are sealed together ultrasonically.

This aspect of the present invention also extends to a method of making such a bag, comprising the steps of (a) folding a sheet of plastics laminate comprising a layer of generally fluid-proof plastics material and a layer of liquid-absorbent plastics material back on itself so that the liquid-absorbent plastics material is on the outside, (b) ultrasonically welding the generally fluid-proof plastics material from the two sides of the sheet thus brought together along at least one seam thereof; and (c) turning the bag thus created inside out to bring the generally fluid-proof plastics material on to the outside with the liquid-absorbent plastics material on the inside.

The first aspect of the present invention also extends to a method of making such a bag comprising the steps of (a) ultrasonically sealing a tubular sheet of a plastics laminate comprising a layer of a generally fluid-proof plastics material and a layer of liquid-absorbent plastics material, with the latter on the outside, to create a seam along one end thereof by sealing together regions of the generally fluid-proof plastics material that are in contact with one another along that seam; and (b) turning the bag thus created inside out to bring the generally fluid-proof plastics material on to the outside with the liquid-absorbent plastics material on the inside A further problem encountered with the waste bag described in EP-B-0 317 047 is that even when the mouth of the bag is carefully gathered and tied, it does not form an adequate seal against the escape of fluids from within the bag.

A second aspect of the present invention seeks to provide a remedy to this problem.

Accordingly, the second aspect of the present invention is directed to a waste bag having an adhesive layer which extends around at least half of the inside of the mouth of the bag, to enable the mouth to be sealed readily after waste matter has been inserted in the bag.

Such a construction is particularly valuable if combined with a waste bag which is made from a sheet of plastics laminate comprising a layer of generally fluid-proof plastics material and a layer of liquid-absorbent plastics material, in which the liquid-absorbent plastics material is on the inside of the bag and the laminate is turned back on itself around the mouth of the bag, the adhesive layer therefore being applied to the generally fluid-proof material around at least half of the inside of the mouth of the bag.

It is desirable for the adhesive layer to extend around slightly more than half of the inside of the mouth of the bag to create a secure seal when the adhesive is used.

Preferably the adhesive layer is protected by a peel-off strip.

Advantageously, the bag has a fold in the laminate to form one side edge of the bag and a seam extending along the other, for example a seam as set out in the first aspect of the present invention. The adhesive layer may then extend between the fold and the seam, preferably slightly beyond both.

An example of a waste bag made in accordance with the present invention will now be described with reference to the accompanying drawings in which.

Figure 1:
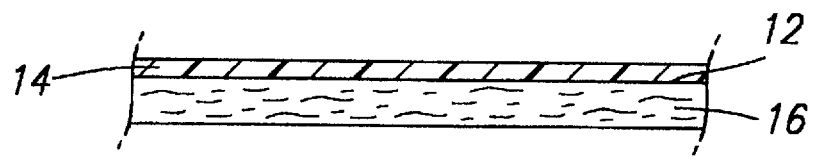
FIG. 1 shows a cross-section through a laminate from which the bag is made.
Figure 4:
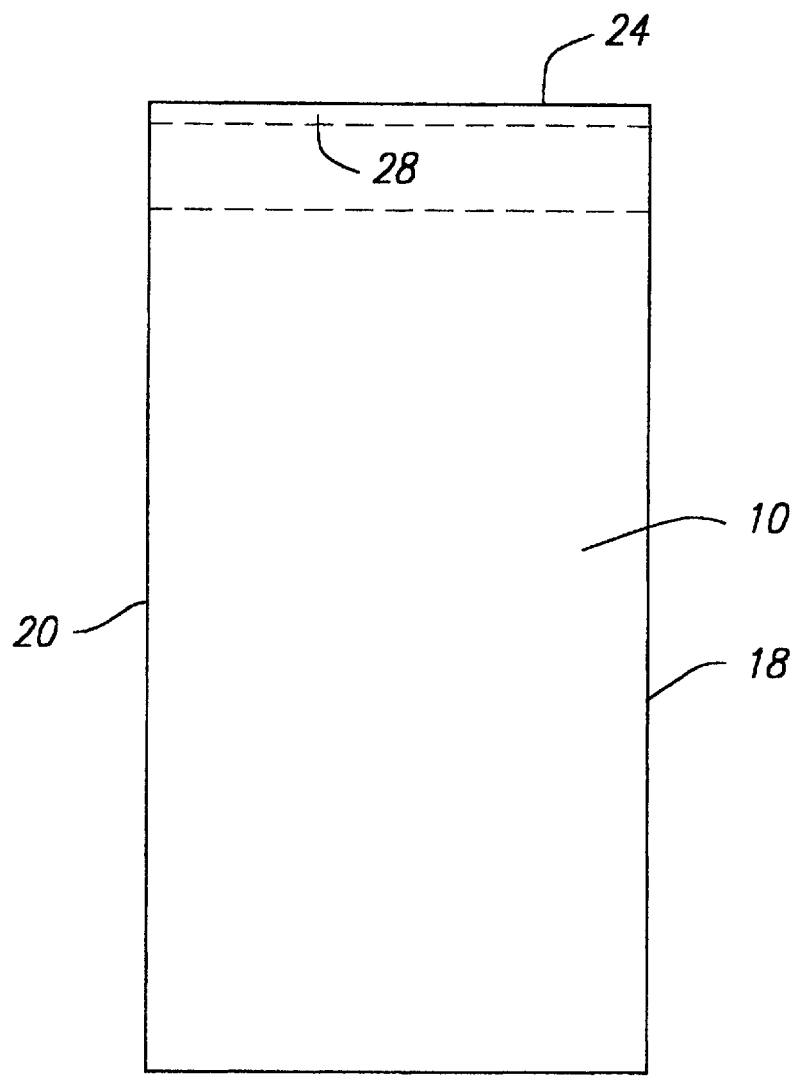
FIG. 4 shows an elevational view of the finished bag.

The waste bag 10 shown as a finished article in FIG. 4 is made from a plastics laminate 12, as shown in FIG. 1. It comprises a generally fluid-proof plastics sheet 14 made of polyethylene laminated to a lining 16 of non-woven liquid-absorbent filamentary polypropylene material.

A generally 110 cm square sheet of the laminate material shown in FIG. 1 is folded on to itself along a fold 18 with the lining 16 at this stage on the outside and the polyethylene layer 14 on the inside. An ultrasonic welder is then used to weld the regions of polyethylene material 14 which are now in contact with one another along lines 20 and 22. The line 20 runs adjacent to the edges of the sheet which have been brought together as a result of the folding of the laminate on to itself, to create a seam 20 along an opposite side edge of the bag to that of the fold 18, all the way from the intended top of the bag to the bottom. The seam 22 extends along an intended bottom of the bag at an opposite end thereof to the intended mouth 24 of the bag, all the way across, so that the seams 20 and 22 cross one another and a complete seal at the intended lower end of the bag and all the way around the sides of the bag is created.

Figure 2:
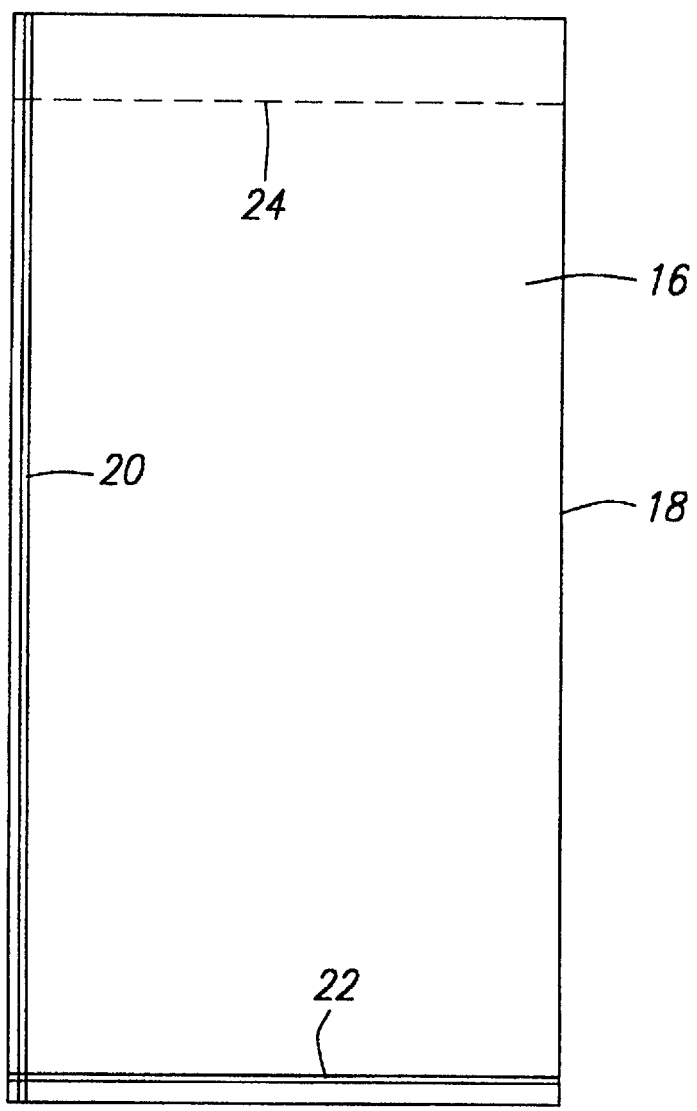
FIG. 2 shows an elevation of an intermediate stage in the manufacture of such a bag.
Figures 3A, 3B:
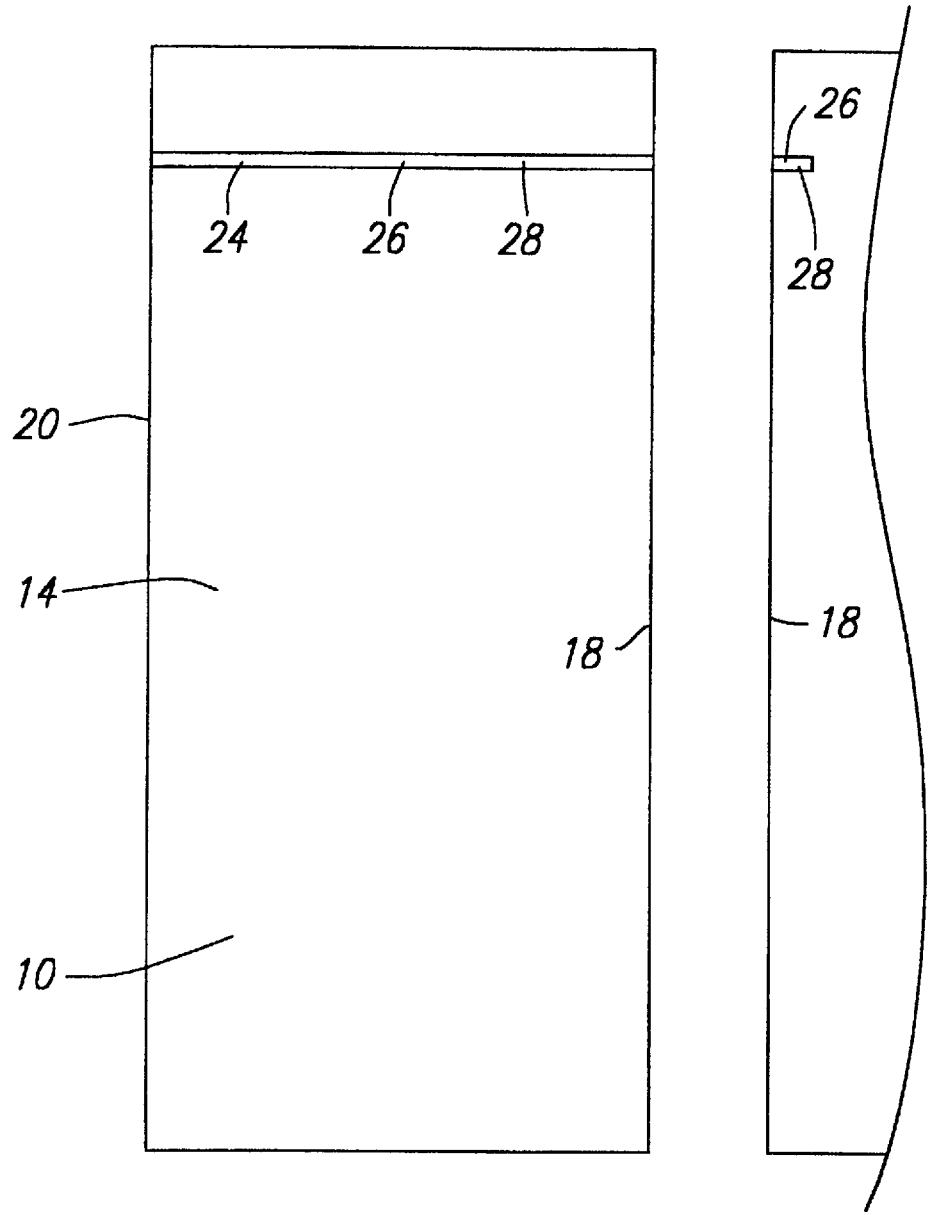
FIGS. 3a and 3b show elevations of respective opposite sides of the bag in a subsequent stage of the manufacture.

The intermediate stage of the bag shown in FIG. 2 is then turned inside out so that the polyethylene layer 14 is now on the outside of the bag. A strip of the polyethylene layer 14 extending immediately below the intended mouth of the bag 24 is coated with a layer of adhesive 26 and, as shown in FIG. 3b, this strip extends around the other side of the bag 10 beyond both side edges 18 and 20. This coating of adhesive material is covered by a protective peel-off strip 28.

Figure 5:
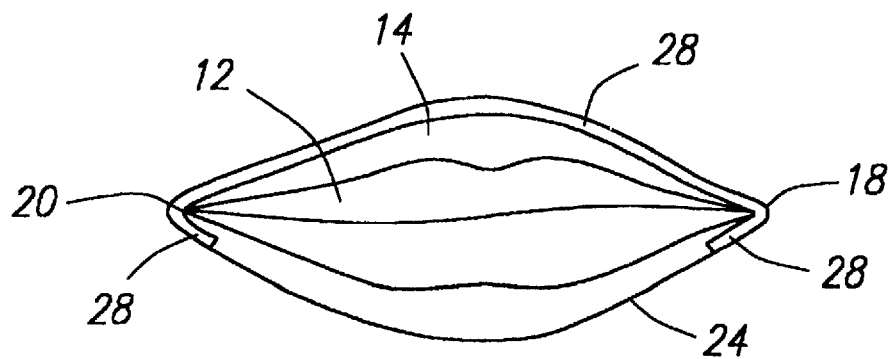
FIG. 5 shows the interior of the mouth of the bag with the latter widened to reveal the various parts thereof.

The bag is completed by folding the mouth end of the bag inwardly on to itself to the line 24 so that the adhesive cover 26 and the peel-off strip 28 are just on the inside of the mouth of the bag 10, as shown in FIG. 4 and perhaps more clearly in FIG. 5.

When the bag is used, waste material, such as discarded medical equipment which may still have body fluid in it, is dropped into the open bag, as shown in FIG. 5, the peel-off strip 28 is removed, and thumb and finger pressure is exerted along the top of the bag at the mouth 24 thereof to press the adhesive layer 26 against the opposite side of the mouth of the bag. This forms a fluid-tight seal even if the bag is accidentally turned upside down. Indeed, the fact that the laminate has been turned in on itself at the mouth of the bag tends to result in fluid and equipment falling into one or other of the pockets created by the inwardly turned mouth, but in the event that any equipment or fluid does find its way between the in-turned sides of the mouth, the seal formed by the adhesive layer 26 is sufficient to prevent leakage, especially because it extends all the way and beyond the side edges of the bag 16 and 20 even before sealing occurs.

Figure 6:
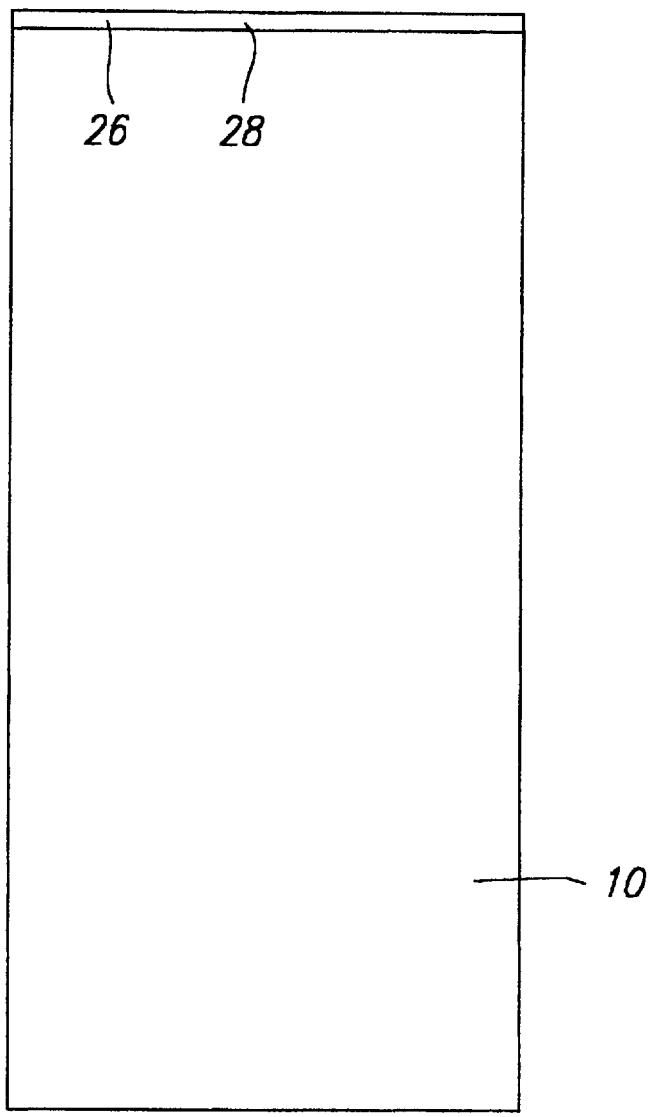
FIG. 6 shows an elevational view of a modified form of such a bag.
Figure 7:
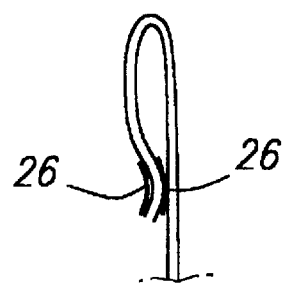
FIG. 7 shows a sectional view through the mouth of the bag shown in FIG. 6 after a first fold.
Figure 8:
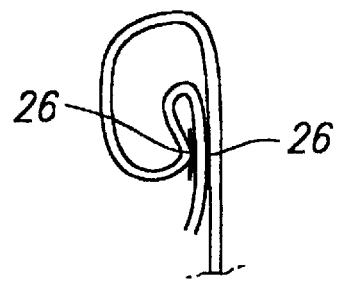
FIG. 8 shoes, on a larger scale, a sectional view through the mouth of the bag shown in FIG. 6 after a second fold.

In the modified bag shown in FIG. 6, the adhesive 26 and peel-off strip 28 (which may be provided by double-sided adhesive tape) is applied around the outside of the bag 10, at the mouth of the bag 10, which in this case is not turned in on itself. Rather, to seal the mouth of the bag, the peel-off strip 28 is removed, and the mouth is folded down on itself by way of a first fold just below the mouth (or just above it after the fold has been completed) so that the adhesive on one side of the mouth adheres to the adjacent side of the bag as shown in FIG. 7, and then a second fold is made between the mouth and the first fold, to fold the bag on itself again, whereby the adhesive on the other side of the mouth adheres to the other side of the bag, as shown in FIG. 8.

Numerous variations and modifications to the illustrated bag may readily occur to a reader of ordinary skill in the art without taking the bag outside the scope of the present invention in one or other of its aspects. For example, the manufacture of the bag may be from a tubular sheet of laminate, and an ultrasonic seal may be formed along the bottom thereof. Indeed, it would be possible to make a bag from a tubular sheet in which both ends may be sealed in the manner in which the mouth only of the bag 10 in the illustrated embodiment is sealed, although such a construction of bag would then fall solely within the scope of the second aspect of the present invention and not the first. The bag may be made in various different sizes.

I claim:

1. A waste bag made from a sheet of plastics laminate comprising a layer of generally fluid-proof plastics material and a layer of liquid-absorbent plastics material, in which the liquid-absorbent material is on the inside of the bag, and along at least one seam of the bag, the laminate is turned back on itself on both sides of the seam so that regions of the generally fluid-proof plastics material on opposite sides of the seam are innermost, with the liquid-absorbent plastics material on the outside thereof, are in contact with one another, and are ultrasonically welded together.

2. The waste bag according to claim 1, having an adhesive layer which extends around at least half of the inside of a mouth of the bag, to enable the mouth to be sealed readily after waste matter has been inserted in the bag.

3. The waste bag according to claim 2, in which the adhesive layer is protected by a peel-off strip.

4. The waste bag according to claim 2, in which the bag has a fold in the sheet of plastics laminate to form one side edge of the bag and a seam extending along the other.

5. The waste bag according to claim 1, having an adhesive layer which extends around the outside of the bag, at a mouth of the bag, to enable the mouth to be adequately sealed readily after waste matter has been inserted in the bag.

6. The waste bag according to claim 5, in which the adhesive layer in protected by a peel-off strip.

7. The waste bag according to claim 5, in which the bag has a fold in the sheet of plastics laminate to form one side edge of the bag and a seam extending along the other.

8. The waste bag according to claim 1, in which the bag has a fold in the laminate to form one side edge of the bag and a seam extending along the other.

9. A method of making a bag according to claim 1, comprising the steps of:
   (a) folding a sheet of plastics laminate comprising a layer of generally fluid-proof plastics material and a layer of liquid-absorbent plastics material back on itself so that the liquid-absorbent plastics material is on the outside;
   (b) ultrasonically welding the generally fluid-proof plastics material from the two sides of the sheet thus brought together along at least one seam thereof; and
   (c) turning the bag thus created inside out to bring the generally fluid-proof plastics material on to the outside with the liquid-absorbent plastics material on the inside.

10. A method of making a bag according to claim 1, comprising the steps of:
   (a) ultrasonically goaling a tubular sheet of a plastics laminate comprising a layer of a generally fluid-proof plastics material and a layer of liquid-absorbent plastics material, with the latter on the outside, to create a seam along one end thereof by sealing together regions of the generally fluid-proof plastics material that are in contact with one another along that seam; and
   (b) turning the bag thus created inside out to bring the generally fluid-proof plastics material on to the outside with the liquid-absorbent plastics material on the inside.

\* \* \* \* \*